(12) United States Patent
Keränen et al.

(10) Patent No.: US 10,130,471 B2
(45) Date of Patent: Nov. 20, 2018

(54) MEDICAL SYSTEM, A DEVICE FOR COLLECTING CHORDAE AND/OR LEAFLETS AND A METHOD THEREFOR

(71) Applicant: Medtentia International Ltd Oy, Helsinki (FI)

(72) Inventors: Olli Keränen, Bjärred (SE); Jani Virtanen, Sipoo (FI); Mark Pugh, Coolaney (IE); Ger O'Carroll, Co. Sligo (IE); Adrian Moran, Co. Sligo (IE)

(73) Assignee: Medtentia International Ltd. Oy, Helsinki (FI)

( * ) Notice: Subject to any disclaimer, the term of this patent is extended or adjusted under 35 U.S.C. 154(b) by 236 days.

(21) Appl. No.: 14/762,428

(22) PCT Filed: Jan. 27, 2014

(86) PCT No.: PCT/EP2014/051541
§ 371 (c)(1),
(2) Date: Jul. 21, 2015

(87) PCT Pub. No.: WO2014/114796
PCT Pub. Date: Jul. 31, 2014

(65) Prior Publication Data
US 2016/0367361 A1      Dec. 22, 2016

Related U.S. Application Data

(60) Provisional application No. 61/756,657, filed on Jan. 25, 2013.

(30) Foreign Application Priority Data

Jan. 25, 2013 (EP) .................................. 13152769

(51) Int. Cl.
A61F 2/24           (2006.01)

(52) U.S. Cl.
CPC .......... *A61F 2/2436* (2013.01); *A61F 2/2412* (2013.01); *A61F 2/2433* (2013.01);
(Continued)

(58) Field of Classification Search
CPC ........ A61F 2/24; A61F 2/2466; A61F 2/2442; A61F 2/2454; A61F 2250/0059
See application file for complete search history.

(56) References Cited

U.S. PATENT DOCUMENTS 6,355,030 B1   3/2002 Aldrich et al.
2007/0038293 A1   2/2007 St. Goar et al.
(Continued)

FOREIGN PATENT DOCUMENTS

WO   WO2012/095159 A2   7/2012

OTHER PUBLICATIONS

WIPO, International Preliminary Examining Authority (European Patent Office), International Preliminary Report on Patentability dated Jun. 5, 2015 in International Patent Application No. PCT/EP2014/051541, 33 pages.
(Continued)

*Primary Examiner* — Diane Yabut
(74) *Attorney, Agent, or Firm* — Inskeep IP Group, Inc.

(57) ABSTRACT

Disclosed is a medical system for short time replacement and repair of a native valve, which comprises an artificial valve (502); and a device for collecting and arranging chordae and/or leaflets to hold and/or stabilize the artificial valve in a desired position, the device comprising: a unit for grasping a plurality of chordae and/or leaflets. The system and/or device allows for fast and easy replacement of a native valve, fast and easy positioning of a temporary artificial valve, and more time for medical personnel to make
(Continued)

decisions, prepare and/or perform surgery/medical intervention.

18 Claims, 10 Drawing Sheets

(52) U.S. Cl.
CPC .......... *A61F 2/2445* (2013.01); *A61F 2/2454* (2013.01); *A61F 2/2466* (2013.01); *A61F 2/2457* (2013.01); *A61F 2250/0059* (2013.01)

(56) References Cited

U.S. PATENT DOCUMENTS

| | | | | |
|---|---|---|---|---|
| 2008/0077235 | A1* | 3/2008 | Kirson | A61F 2/2409 623/2.11 |
| 2009/0043381 | A1* | 2/2009 | Macoviak | A61B 17/00234 623/2.36 |
| 2010/0331971 | A1 | 12/2010 | Keränen et al. | |
| 2011/0137410 | A1* | 6/2011 | Hacohen | A61F 2/2412 623/2.37 |
| 2011/0224655 | A1 | 9/2011 | Asirvatham et al. | |
| 2012/0022640 | A1 | 1/2012 | Gross et al. | |
| 2012/0035721 | A1 | 2/2012 | Vesely | |
| 2013/0006352 | A1* | 1/2013 | Yaron | A61F 2/2445 623/2.37 |
| 2014/0194975 | A1* | 7/2014 | Quill | A61F 2/2427 623/2.11 |

OTHER PUBLICATIONS

WIPO, European International Search Authority, International Search Report dated Feb. 28, 2014 in International Patent Application No. PCT/EP2014/051541, 6 pages.

* cited by examiner

MEDICAL SYSTEM, A DEVICE FOR COLLECTING CHORDAE AND/OR LEAFLETS AND A METHOD THEREFOR

RELATED APPLICATIONS

This application is the U.S. National Phase of and claims priority to International Patent Application No. PCT/EP2014/051541, International Filing Date Jan. 27, 2014, entitled A Medical System, A Device For Collecting Chordae And/Or Leaflets And A Method Therefor, which claims benefit of European Application No. EP13152769.9, filed Jan. 25, 2013 entitled A Medical System, And A Device For Collecting Chordae And/Or Leaflets; and U.S. Provisional Application Ser. No. 61/756,657, filed Jan. 25, 2013 entitled A Medical System, A Device For Collecting Chordae And/Or Leaflets And A Method Therefor; all of which are incorporated herein by reference in their entireties.

This application is related to application "A medical device and method for facilitating selection of an annuloplasty implant" filed Jan. 25, 2013 having EP application nr: EP13152774 and U.S. provisional application No. 61/756,633, application "A valve for short time replacement for taking over the function of, and/or for temporary or partial support of, a native valve in a heart" filed Jan. 25, 2013 having EP application nr: EP13152770 and U.S. provisional application No. 61/756,649, application "Temporary atrium support device" filed Jan. 25, 2013 having EP application nr: EP13152771 and U.S. provisional application No. 61/756,663, and application "A system for cardiac valve repair" filed Jan. 25, 2013 having EP application nr: EP13152768 and U.S. provisional application No. 61/756,670. The above applications are incorporated herein by reference in their entirety for all purposes.

BACKGROUND OF THE INVENTION

Field of the Invention

This invention pertains in general to the field of medical devices for improvement of heart valves, such as mitral, aortic or tricuspid valves, as well as tools and methods therefore. More particularly the invention relates to a medical system for short time replacement, support and/or repair of a native valve, a device for collecting and arranging chordae and/or leaflets to hold and/or stabilize an artificial valve in a desired position and a method of delivering an artificial valve for short time replacement of a native valve in a heart.

Description of the Prior Art

During heart surgery, a premium is placed on reducing the amount of time used to replace and repair valves as the heart is frequently arrested and without perfusion.

Thus, it would be advantageous to have an artificial valve temporarily replacing a native valve to be repaired or replaced during the repair or replacement.

Furthermore, since a premium is placed on reducing the amount of time used to replace and/or repair valves, there is not a lot of time for making decisions, preparing and/or performing surgery/medical intervention. Thus, it would also be advantageous to have more time to make decisions, for preparations and/or for performing surgery or medical intervention. This may be important, especially since it will lead to an improved quality of the replacement or repair.

The use of an artificial valve has been disclosed in US20070219630 A1. However, as can be seen from e.g. FIG. 5 and [0129] in this document, the temporary valve is placed away from the mitral valve. Furthermore, as can be seen in [0075] of this document, a mitral valve separation unit is needed for proper function. Moreover, the flow is in the embodiments described in this document directed through conduits (refer to e.g. conduits 130, 140, 330, 340, 430, 440) and thus not through the native valve.

The construction of the temporary valve function as a whole is thus rather complicated. Furthermore, since the artificial valve is placed away from the native valve, it cannot utilize parts of the native valve for e.g. positioning and securing of the artificial valve.

In WO2012/095159 A2 a ring-shaped prosthetic valve is disclosed for permanently replacing an atrioventricular heart valve that comprises an annular body on which valvular cusps are fastened for insertion into a valve annulus of the heart.

In US2007/255396 A1 a girdle is disclosed for surrounding the chordae tendinae of a heart valve.

In US2007/038293 A1 a device and methods for endoscopic annuloplasty are disclosed. Opposed valve leaflets may be temporarily grasped and held into position prior to permanent attachment. No replacement valve is disclosed in US2007/038293 A1.

It may thus be advantageous to have a temporary valve which is of a simple and cost-effective construction. It may further be advantageous to have means for fast and easy fixation and stabilization of an artificial valve for temporary use. Furthermore, it may be advantageous to have means for fast and/or easy temporary replacement of a native valve. Moreover, it may be advantageous to have means for fast and easy positioning of a temporary artificial valve. In addition, it may be advantageous to have means for collecting and arranging chordae to hold and/or stabilize the artificial valve in a desired position.

Hence, an improved system or device would be advantageous and in particular a system or device for repair and/or replacement of a native valve allowing for increased flexibility and cost-effectiveness.

SUMMARY OF THE INVENTION

Accordingly, examples of the present invention preferably seek to mitigate, alleviate or eliminate one or more deficiencies, disadvantages or issues in the art, such as the above-identified, singly or in any combination by providing a medical system, a device for collecting chordae and method therefor, according to the appended patent claims.

According to aspects of the disclosure, a medical system and a device for collecting chordae and/or leaflets as well as a method of delivery therefor are disclosed, whereby fast and easy replacement of a native valve, fast and easy positioning of a temporary artificial valve, and improved quality of repair and/or replacement of a native valve may be achieved.

According to one aspect of the disclosure, a medical system for short time replacement and repair of a native valve is provided. The system comprises an artificial valve and a device for collecting and arranging chordae and/or leaflets to hold and/or stabilize the artificial valve in a desired position. The device comprises a unit for grasping a plurality of chordae and/or leaflets.

According to another aspect of the disclosure, a device for collecting and arranging chordae and/or leaflets to hold and/or stabilize an artificial valve in a desired position is provided. The device comprises a unit for grasping a plurality of chordae and/or leaflets.

According to yet another aspect of the disclosure, a method of delivering an artificial valve for short time replacement of a native valve, such as a mitral valve or an aortic valve, in a heart is provided. The method comprises positioning the artificial valve inside the native valve. The method further comprises pulling a plurality of chordae and/or leaflets together and towards the artificial valve for fixation of the artificial valve. The method also comprises deploying a clip to surround the artificial valve and/or to keep the chordae and/or leaflets in position towards the artificial valve. The method may also comprise gaining trans-apical access to the heart. Furthermore, the method may comprise forwarding a catheter, via a trans-apical route, into the left ventricle of the heart. Alternatively, the method may comprise forwarding a catheter, via an aortic route into the ascending aorta of said heart (12). Moreover, the method may comprise passing the catheter at least partly through the native valve. In addition, the method may comprise removing the catheter.

Further examples of the disclosure are defined in the dependent claims, wherein features for the second and subsequent aspects of the disclosure are as for the first aspect mutatis mutandis.

Some examples of the disclosure provide for more time for making decisions about how to perform surgery.

Some examples of the disclosure provide for more time for preparing surgery.

Some examples of the disclosure provide for more time for performing surgery or medical intervention.

Some examples of the disclosure provide for an improved quality of repair or replacement of a native valve.

Some examples of the disclosure provide for a simple and/or a reliable temporary valve function.

Some examples of the disclosure provide for that the tube does not interfere with annuloplasty.

Some examples of the disclosure provide for reliable securing of the temporary valve.

Some examples of the disclosure provide for fast and/or easy replacement of a native valve.

Some examples of the disclosure provide for fast and/or easy positioning of a temporary valve.

Some examples of the disclosure provide for that simple and/or fast deployment of a clip is enabled.

Some examples of the disclosure provide for a fast and easy collection of chordae.

Some examples of the disclosure provide for fast and easy securing of the temporary valve.

Some examples of the disclosure provide for fast and easy tightening to minimize paravalvular leakage.

Some examples of the disclosure provide for a procedure that is less prone to errors, and thus a faster and easier securing of the valve.

Some examples of the disclosure provide for reliable securing of valve and chordae.

Some examples of the disclosure enable precise positioning of an implant or a valve in the anatomically correct position.

Some examples of the disclosure provide for that the procedure or surgery can be performed with high accuracy.

Some examples of the disclosure provide for an easier and/or less invasive delivery method.

Some examples of the disclosure provide for fast and easy collection of chordae.

Some examples of the disclosure provide for a fast and easy way of delivering, positioning and/or securing a temporary valve from outside the body of a patient.

Some examples of the disclosure provide for a reliable securing of a temporary valve and chordae.

Some examples of the disclosure enable beating heart surgery.

Some examples of the disclosure provide for a reduced leakage.

Some examples of the disclosure provide for a minimized regurgitation during e.g. beating heart surgery.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the invention are capable of will be apparent and elucidated from the following description of examples of the present invention, reference being made to the accompanying drawings, in which.

DESCRIPTION OF THE PREFERRED EXAMPLES

Figure 1A:
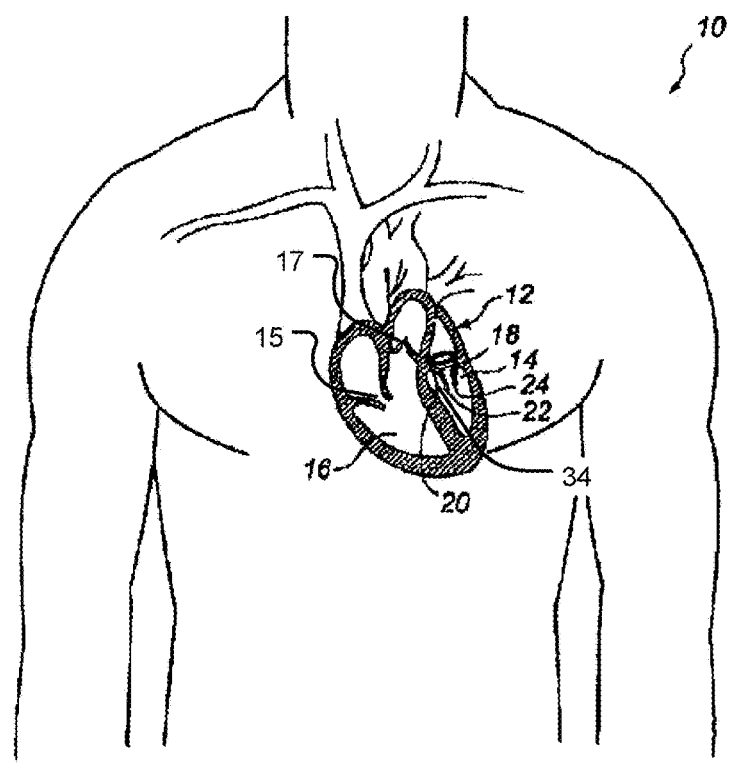
FIG. 1A is a schematic cross-sectional view of a patient with a heart.

Specific examples of the invention will now be described with reference to the accompanying drawings. This invention may, however, be embodied in many different forms and should not be construed as limited to the examples set forth herein. Rather, these examples are provided so that this disclosure will be thorough and complete, and will fully convey the scope of the invention to those skilled in the art. The terminology used in the detailed description of the examples illustrated in the accompanying drawings is not intended to be limiting of the invention. In the drawings, like numbers refer to like elements.

The following description focuses on an example of the present disclosure applicable to a native valve of the heart and in particular to a mitral and an aortic valve. However, it will be appreciated that the disclosure is not limited to this application but may be applied to many other native valves including for example a tricuspid valve or a pulmonary valve.

Figure 1B:
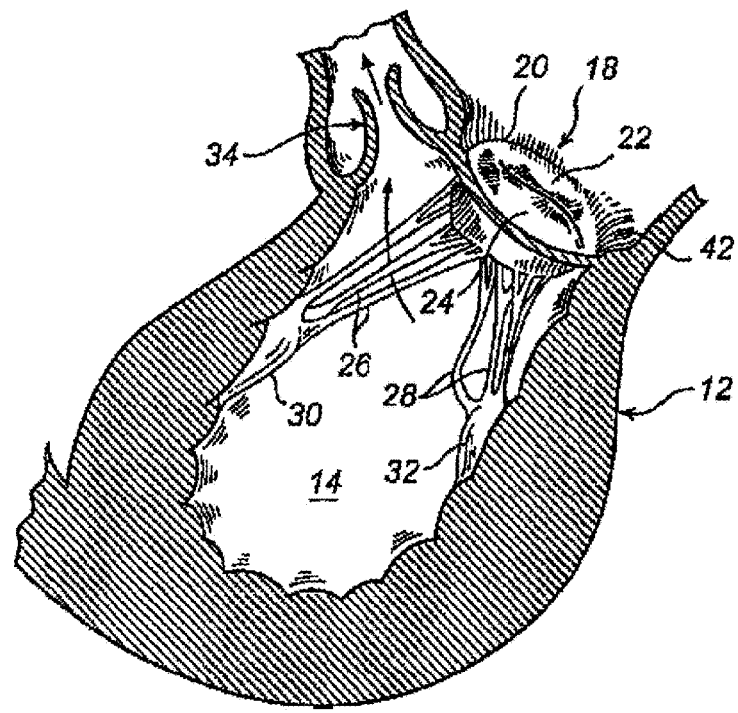
FIG. 1B is a schematic perspective view of a mitral valve and an aortic valve.

FIG. 1A illustrates a patient 10 having a heart 12 shown in cross-section including a left ventricle 14 and a right ventricle 16. The concepts of the present disclosure are suitable to be applied, for example, to a mitral valve 18, which supplies blood into the left ventricle 14 or to an aortic valve 34. The tricuspid valve (15) and the pulmonary valve (17) are also shown in FIG. 1A. Native mitral valve 18, also shown in FIG. 1B, includes an annulus 20 and a pair of leaflets 22, 24 which selectively allow and prevent blood flow into the left ventricle 14. Leaflets 22, 24 are supported for coaptation by chordae tendinae, chordae or chords 26, 28 extending upwardly from respective papillary muscles 30, 32. Blood enters the left ventricle 14 through the mitral valve 18 and is expelled during subsequent contraction of heart 12 through aortic valve 34. The aortic valve 34 controls blood flow to the aorta and organs connected to the aorta. It will be appreciated that the present disclosure may also be applicable to a tricuspid heart valve (15).

Figure 2:
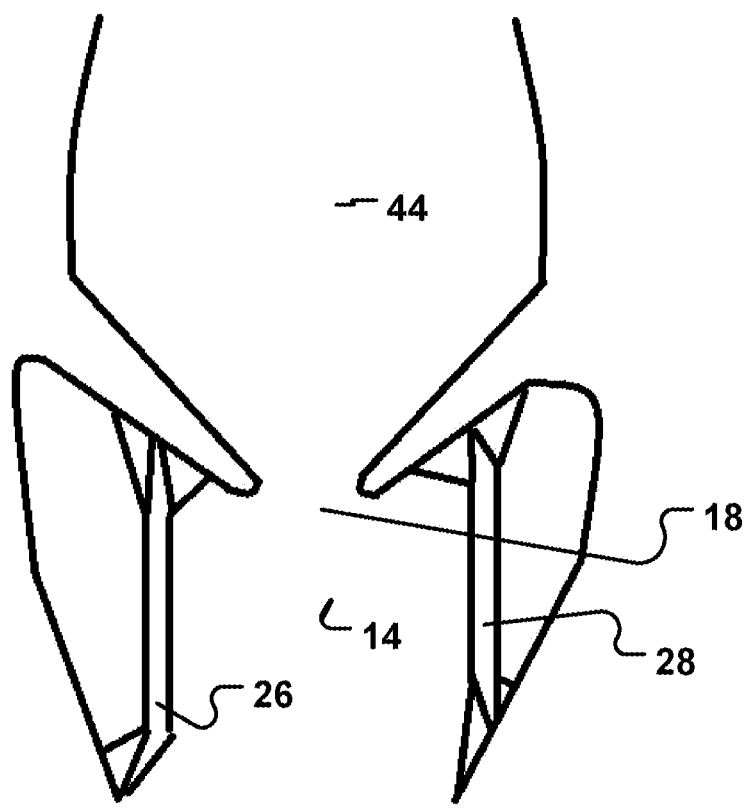
FIG. 2 is a schematic cross-sectional view of a mitral valve.

FIG. 2 is a cross-sectional view of a mitral valve 18 and surroundings. The left atrium 44, the left ventricle 14, the chordae 26, 28 and the mitral valve 18 can be seen in this figure.

Figure 3A:
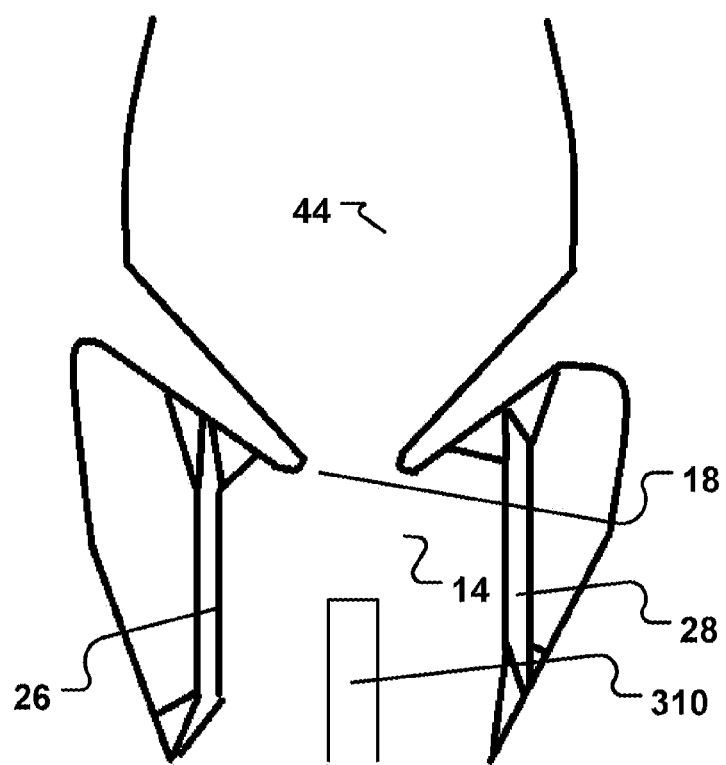
FIG. 3A is a schematic cross-sectional view of a mitral valve with a catheter inserted into the left ventricle.

FIG. 3A illustrates a catheter 310, which is being utilized for delivering a valve for short time replacement of a native valve, such as the mitral valve 18. The catheter 310 may be inserted into the left ventricle 14 of the heart in any known way. The catheter 310 is in some examples inserted via a transapical route. In these examples trans-apical access to the heart is gained and the catheter 310 will be forwarded, via the trans-apical route, into the left ventricle 14 of the heart.

Figure 4A:
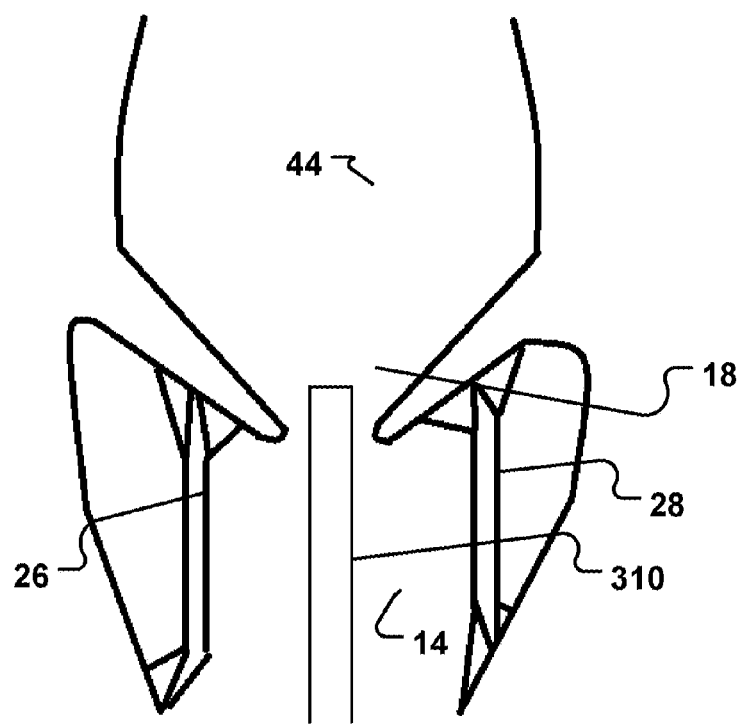
FIG. 4A is a schematic cross-sectional view of a mitral valve with a catheter partly in the left atrium.
Figure 5A:
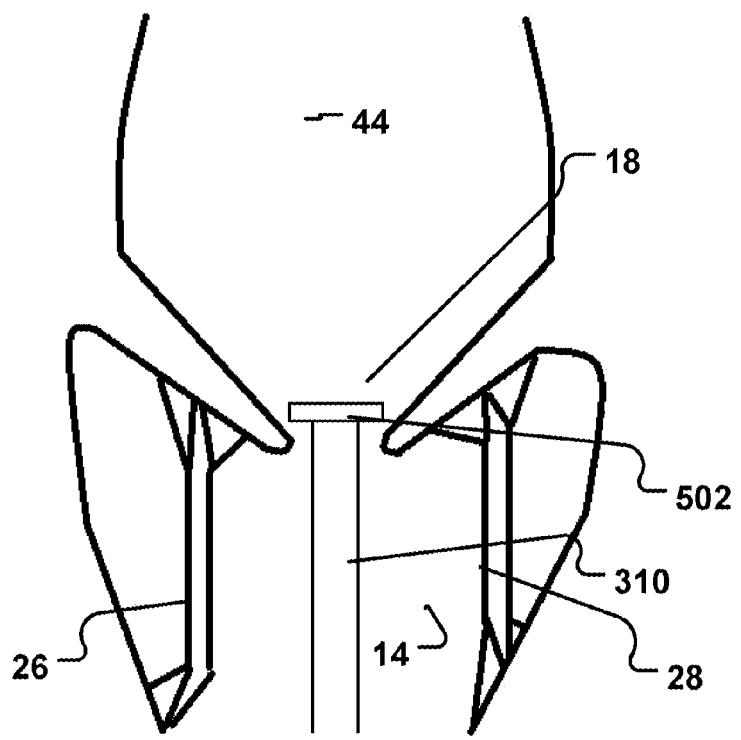
FIG. 5A is a schematic cross-sectional view of a mitral valve with a valve being delivered.

Once the catheter has entered the left ventricle 14, the catheter is forwarded so that it is at least partly put through the mitral valve 18 and partly into the left atrium 44 as illustrated in FIG. 4A. The catheter 310 may be the delivery system for all implements used in the procedure. Thus, the catheter 310 may be utilized also for delivery of chordae collection devices, commissure locating tools and/or annuloplasty devices for long-term use. Thereafter, the valve for short-time replacement 502, which may be an artificial valve, is positioned inside the native mitral valve 18. This is illustrated in FIG. 5A. In order to facilitate the delivery of the valve 502 and to enable the positioning of the valve 502, the valve 502 may be collapsible for delivery and/or expandable upon delivery. This may be achieved by the use of an at least partly flexible valve. As an example, a flange of the valve 502 may be flexible during delivery. Once the valve 502 has been positioned inside the native valve, a plurality of chordae may be pulled together and towards the valve 502 for fixation of the valve 502.

Pulling of a plurality of chordae together is in some examples performed for creation of a temporary space between at least one chorda and a ventricular wall of the heart. Within this temporary space, an annuloplasty device may pass for delivery. Thus, an additional space may be created between e.g. at least two chordae and a ventricular wall of the heart by pulling a plurality of chordae together. Through the additional space an annuloplasty device may be advanced into position. The insertion of an annuloplasty device is preferably performed after the valve 502 has been positioned.

The plurality of chordae may in some examples be pulled together by rotation or twisting of the valve 502. The rotation of the valve 502 for pulling the chordae together is preferably specified to one direction, such as anticlockwise rotation. The rotation of the valve 502 may be actuated by rotating a catheter. As an example, a two-axis steerable catheter may be used for actuating the rotation of the valve 502.

A clip may thereafter be deployed to surround the valve 502 and/or to keep the chordae in position towards the valve 502. In some examples, the clip is deployed by pushing it out of the catheter 310 and into position with a pusher or a pushing catheter. Alternatively or in addition, the clip may be delivered with a special clip guide tube. The catheter 310 may thereafter be removed or utilized for inserting further implants or devices, such as an annuloplasty device. The valve 502 may remain inside the native valve during positioning of an annuloplasty device. Once an annuloplasty device has been inserted for permanent implantation, positioned and secured, the temporary, short-term, valve 502 is removed.

Figure 3B:
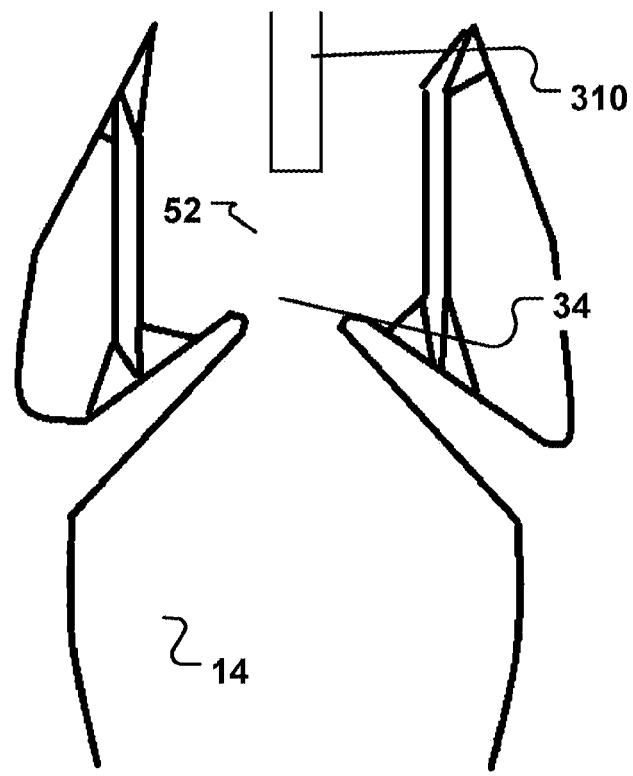
FIG. 3B is a schematic cross-sectional view of an aortic valve with a catheter inserted into the aortic arc and partly into the ascending aorta.

FIG. 3B illustrates a catheter 310, which is being utilized for delivering a valve for short time replacement of a native valve, such as the aortic valve 34. The catheter 310 may be inserted via the aortic arc at least partly into the ascending aorta 52. In these examples, the catheter enters for instance trans-femorally from the groin and goes via aorta at least partly into the ascending aorta 52 for delivery of the valve at the aortic valve 34.

Figure 4B:
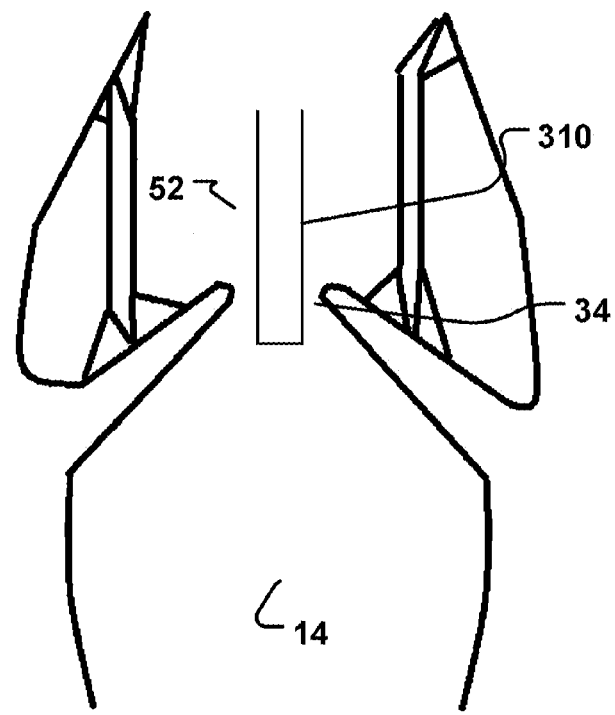
FIG. 4B is a schematic cross-sectional view of an aortic valve with a catheter partly in the ascending aorta.
Figure 5B:
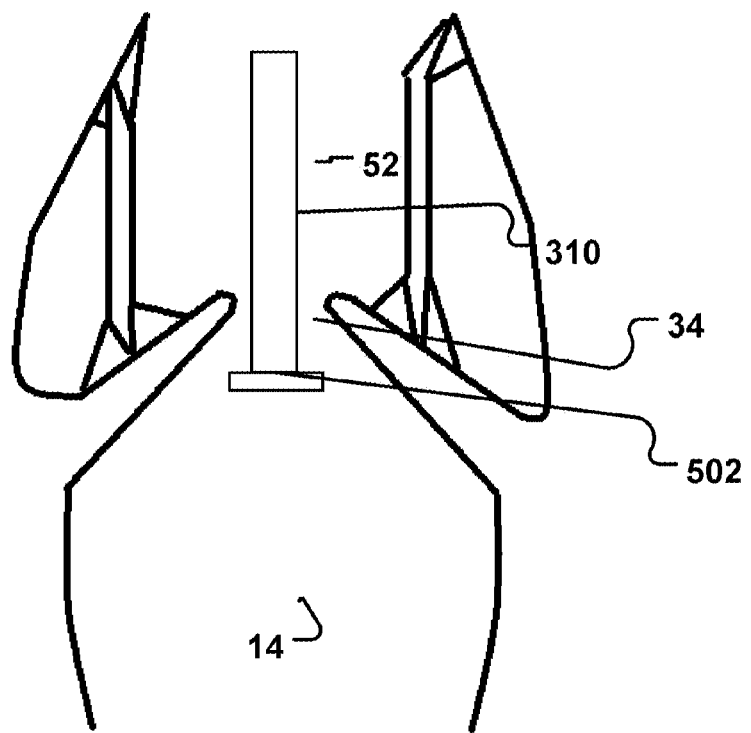
FIG. 5B is a schematic cross-sectional view of an aortic valve with a valve being delivered.

Once the catheter has entered the ascending aorta 52, the catheter is forwarded so that it is at least partly put through the aortic valve 34 and partly into the left ventricle 14 as illustrated in FIG. 4B. The catheter 310 may be the delivery system for all implements used in the procedure. Thus, the catheter 310 may in addition be utilized also for delivery of chordae collection devices, commissure locating tools and/or annuloplasty devices for long-term use. Thereafter, the valve for short-time replacement 502, which may be an artificial valve, is positioned inside the native aortic valve 34. This is illustrated in FIG. 5B. In order to facilitate the delivery of the valve 502 and to enable the positioning of the valve 502, the valve 502 may be collapsible for delivery and/or expandable upon delivery. This may be achieved by the use of an at least partly flexible valve. As an example, a flange of the valve 502 may be flexible during delivery. Once the valve 502 has been positioned inside the native valve, a plurality of chordae may be pulled together and towards the valve 502 for fixation of the valve 502.

Pulling of a plurality of chordae together is in some examples performed for creation of a temporary space between at least one chorda and a ventricular wall of the heart. Within this temporary space, an annuloplasty device may pass for delivery. Thus, an additional space may be created between e.g. at least two chordae and a ventricular wall of the heart 12 by pulling a plurality of chordae together. Through the additional space an annuloplasty device may be advanced into position. The insertion of an annuloplasty device is preferably performed after the valve 502 has been positioned.

The plurality of chordae may in some examples be pulled together by rotation or twisting of the valve 502. The rotation of the valve 502 for pulling the chordae together is preferably specified to one direction, such as anticlockwise rotation. The rotation of the valve 502 may be actuated by rotating a catheter. As an example, a two-axis steerable catheter may be used for actuating the rotation of the valve 502.

A clip may thereafter be deployed to surround the valve 502 and/or to keep the chordae in position towards the valve 502. In some examples, the clip is deployed by pushing it out of the catheter 310 and into position with a pusher or a pushing catheter. Alternatively or in addition, the clip may be delivered with a special clip guide tube. The catheter 310 may thereafter be removed or is alternatively utilized for inserting further implants or devices, such as an annuloplasty device. The valve 502 may remain inside the native valve during positioning of an annuloplasty device. Once an annuloplasty device has been inserted, positioned and secured, the valve 502 is removed.

Figure 6A:
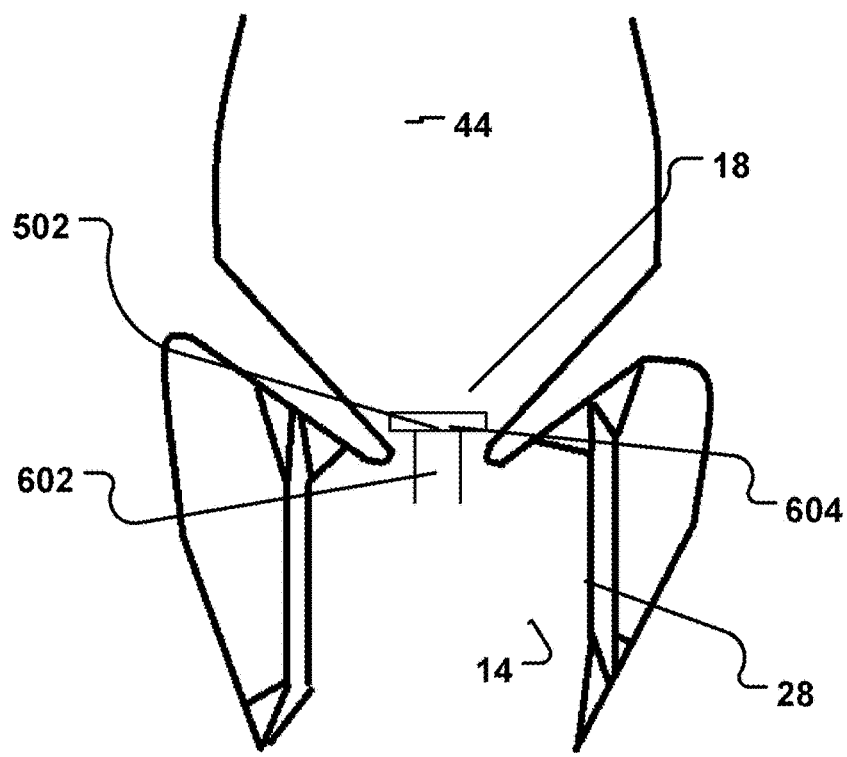
FIG. 6A is a schematic cross-sectional view of a mitral valve with a valve for short time replacement of the mitral valve.
Figure 6B:
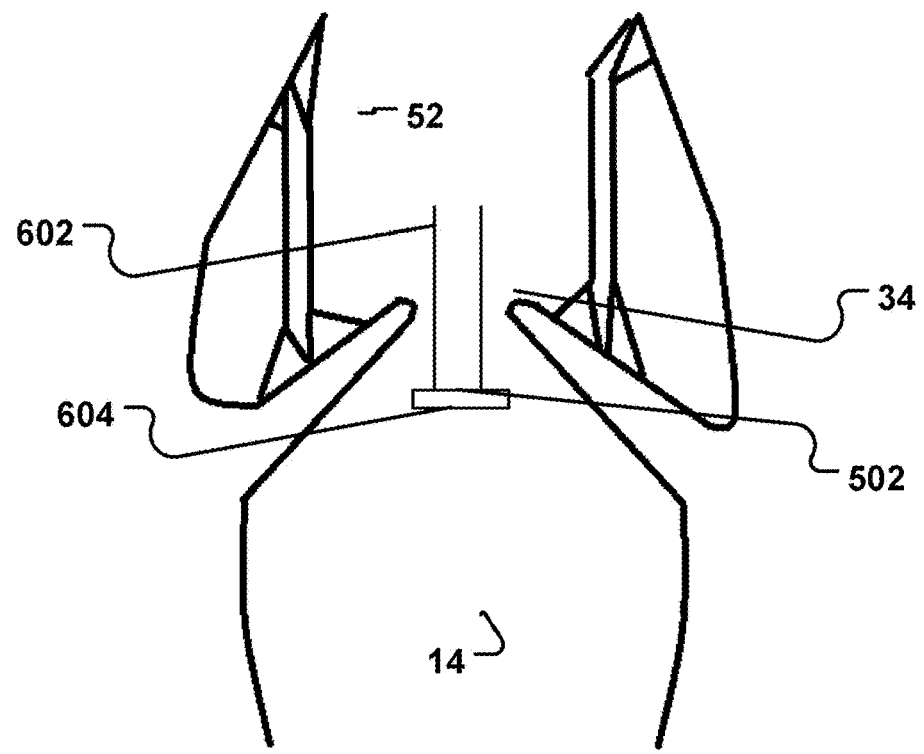
FIG. 6B is a schematic cross-sectional view of an aortic valve with a valve for short time replacement of the aortic valve.

The valve 502, shown in FIGS. 6A and 6B, is for short time replacement of a native valve in a heart and the valve 502 may be positioned through the native valve upon implantation. The valve 502 comprises an at least partially collapsible and/or at least partially expandable tube 602. Furthermore, the valve 502 comprises a flange 604. The flange 604 may be flexible during delivery, and is preferably somewhat rigid once the valve 502 has been implanted. The flange 604 prevents the valve 502 from moving out of position from e.g. the left atrium 44 towards the left ventricle 14 if the valve is for the mitral valve 18 and from moving out of position from e.g. the ascending aorta towards the aortic arc if the valve is for the aortic valve 34.

Figures 7A, 7B, 7C:
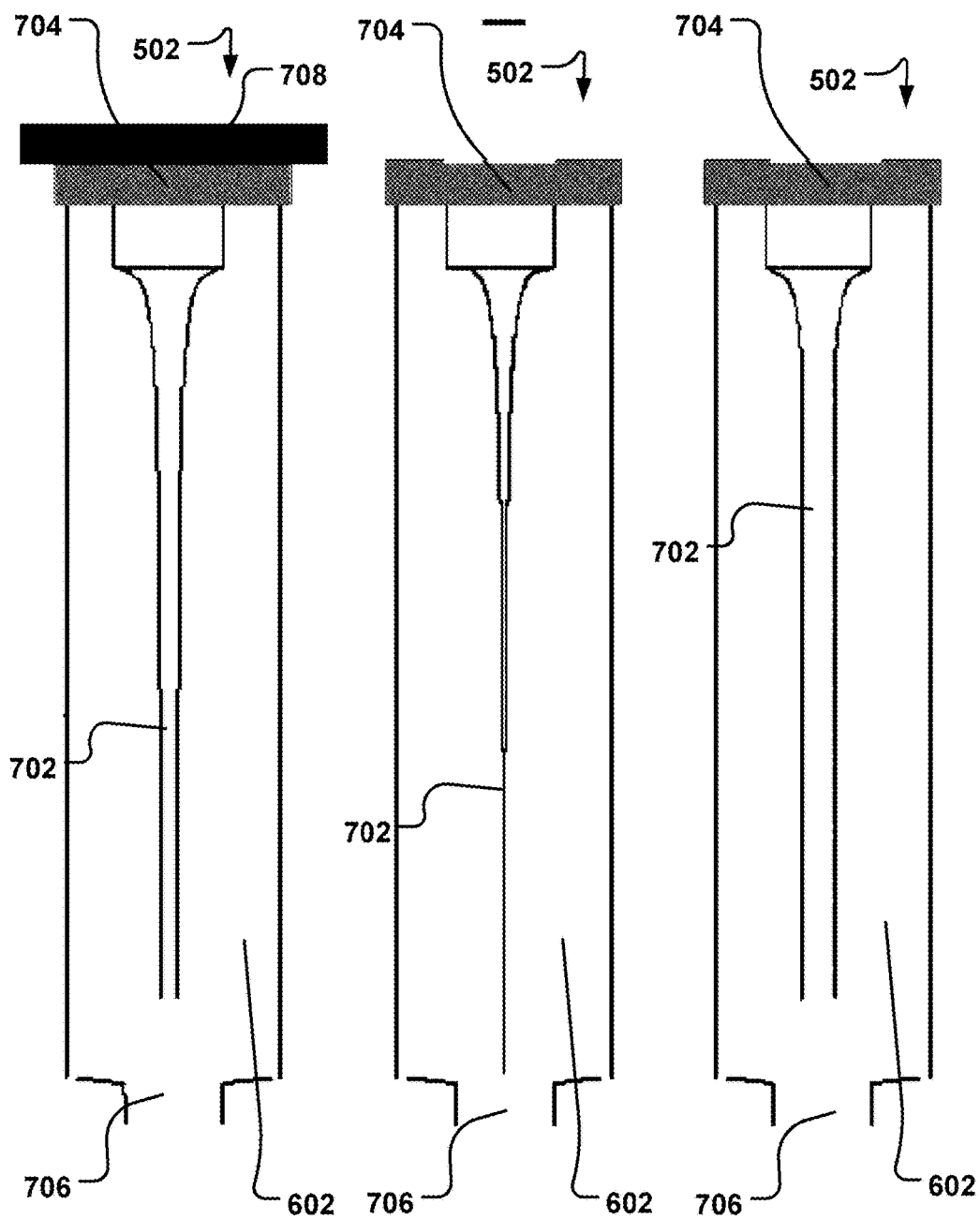
FIG. 7A-C are schematic illustrations of a principle of a valve for short time replacement of a native valve.

In some examples, the valve 502 is a one-way valve comprising a tube 602 having an inlet side 704 and an outlet side 706. This is depicted in FIG. 7A-C. The tube 602 may be flexible. This may be advantageous, since the use of a flexible tube prevents interference between the tube 602 and annuloplasty devices. Alternatively, the tube 602 may be rigid or at least somewhat rigid. The valve 502 may further comprise a flexible inner sleeve 702 attached to an inlet side 704 of the tube 602 and positioned inside the tube 602. This is depicted in FIG. 7A. The flexible inner sleeve 702 may be made of a flexible material such as rubber. In FIG. 7A, the pressure inside the tube 602 is similar to the pressure at the inlet side 704 of the tube 602. Therefore, the flexible inner sleeve 702 has more or less a same pressure on an inside of the sleeve 702 which is in contact with the inlet side 704, as on an outside of the flexible inner sleeve 702 which is in contact with the outlet side 705, thus making the valve partly open. In FIG. 7b the pressure inside the tube 602 has increased so that the pressure inside the tube 602, outside of the flexible inner sleeve 702 and in the left ventricle 14 is larger than the pressure at the inlet of the tube 602, inside of the flexible inner sleeve 702 and the left atrium 44. When the pressure inside the tube 602 becomes higher than the pressure at and/or outside the inlet of the tube, the valve 502 closes by the flexible inner sleeve 702 contracting together. In FIG. 7C the pressure inside the tube 602 and outside of the flexible inner sleeve 702 is lower than the pressure at or outside the inlet of the tube 704 and inside of the flexible inner sleeve 702. When the pressure inside the tube 602 becomes lower than the pressure at or outside the inlet of the tube, the valve 502 and flexible inner sleeve 702 opens.

Thus, a simple, yet reliable replacement valve is obtained by the construction of a valve 502 as illustrated in FIGS. 7A-7C. The flange 708 can also be seen in FIG. 7A. The flange 708 may be expandable. In one example, the flange 708 is an expandable balloon.

Figure 8A:
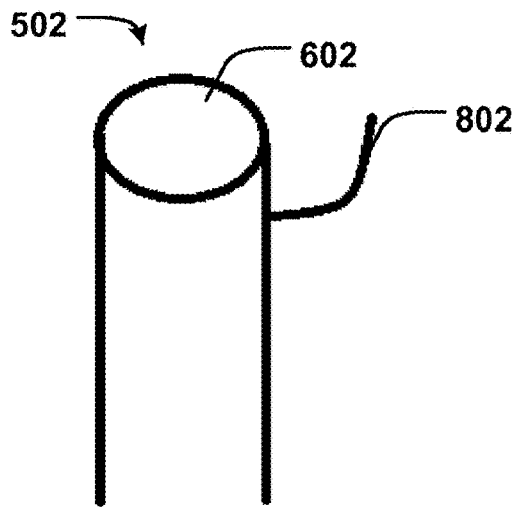
FIGS. 8A-B are schematic perspective views of a collecting unit for collecting and arranging chordae towards a valve.
Figure 8B:
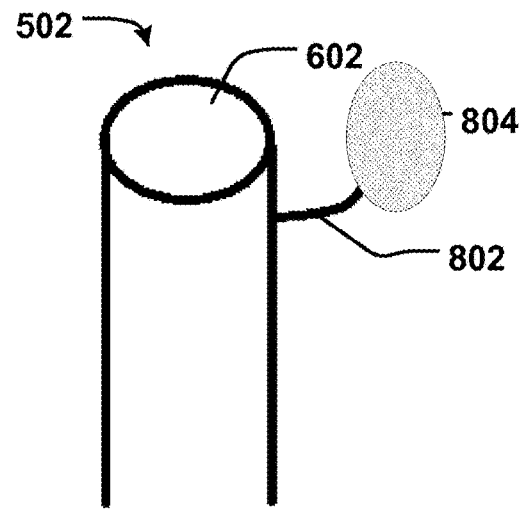

FIG. 8A illustrates an example, wherein a collecting unit 802 is utilized for collecting and arranging chordae towards the valve 502. The collecting unit 802 may together with the tube 602 form one integral part. Alternatively, the collecting unit 802 may be attachable or attached to the tube 602. In some examples, the collecting unit 802 comprises a single arm or a single hook. Alternatively or in addition, the collecting unit 802 comprises a ring and/or a fluid-filled balloon. A collection unit 802 comprising a fluid-fillable or fluid-filled balloon 804 is depicted in FIG. 8B. The collection unit 802 may in addition to the fluid-fillable or fluid-filled balloon 804 comprise a single arm.

In some examples the valve 502 comprises the collecting unit 802 for collecting and arranging chordae towards the valve 502. The valve may be secured, held and/or stabilized in a desired position by the collecting and arranging of chordae towards the valve 502. Thus, a reliable securing of the valve 502 may be achieved.

By the use of a collecting unit 802, fast and easy replacement of a native valve may be achieved. Furthermore, fast and easy positioning of a temporary valve may be obtained. Therefore, the use of a collecting unit may contribute to give more time to make decisions related to surgery, more time to prepare for surgery and/or more time to perform surgery or medical intervention. Thus, overall quality of valve replacement or repair may be improved. The securing of the valve with chordae together with the shape of the valve 502 and a correct dimensioning of the valve 502 may be advantageous, since a valve with proper dimensions secured by the chordae does not press against any ventricular wall. Thus, there will be no damage to the ventricular walls. Although, there may be a small leakage outside the valve 502, this may be acceptable for a short period of time, such as minutes, hours or a few days.

Figure 9:
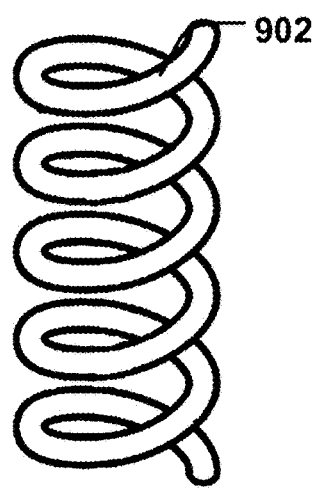
FIG. 9 is a schematic view of a clip used to secure a valve.

The valve may thus in certain examples include a collecting unit for collecting and arranging chordae towards the valve. The valve is thus secured, held and/or stabilized in a desired position by the collecting unit and arranging of chordae towards said valve. In an example the collecting unit includes a clip, wherein the chordae and/or leaflets are kept in position towards the valve with said clip. The clip may form a helix. The clip, in particular when in form of a helix, may be integral with or connected to the collecting unit and not a separate piece. Hence, in some examples, the collecting unit 802 may comprise a clip. FIG. 9 illustrates such a clip 902. The chordae are kept in position towards the valve 502 with the clip 902. The clip 902 may be formed as a ring or ring-like structure. Alternatively, the clip 902 may be formed or shaped as a helix. Thereby, the clip 902 can easily be rotated into position. Rotation is preferably made together with the valve when the collecting unit, such as a clip, in particular when in form of a helix, is integral with the collecting unit. The chordae and/or leaflets are the kept in position towards the valve with said collecting unit and secured with said clip. This may be advantageous, since a simple and/or fast deployment of the clip 902 is enabled thereby. Furthermore, reliable securing, simple and/or fast deployment of a clip is enabled. Alternatively, when the clip, in particular when in form of a helix, is a separate piece and not integral with or unconnected with the valve, the collecting unit may be rotated separately into position. The clip may then be applied to the collecting unit for securing the latter in position at the chordae and/or leaflets.

Figure 10:
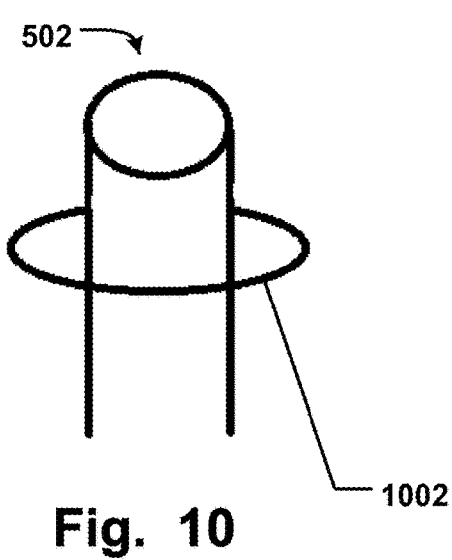
FIGS. 10 and 11 are perspective views of various collecting units for collecting and arranging chordae towards a valve.

FIG. 10 illustrates a valve 502 having a collecting unit for collecting and arranging chordae towards the valve 502 according to some examples. In these examples the collecting unit is shaped as a ring or ring-like structure. The ring-shaped unit 1002 may be extended to a rod-like structure for delivery and changeable into a ring-like structure upon delivery or implantation. Thus, it may be advantageous to have a collecting unit shaped as a ring, since it may facilitate delivery.

Figure 11:
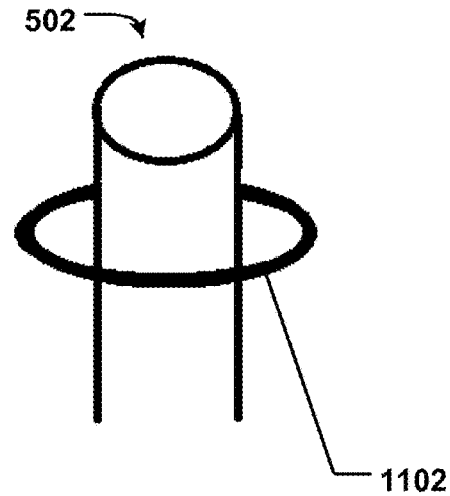

FIG. 11 illustrates a valve 502 having a collecting unit for collecting and arranging chordae towards the valve 502 according to some examples. In these examples the collecting unit is a fluid-filled balloon 1102. The fluid-filled balloon 1102 may be ring-like The use of a fluid-filled balloon 1102 as a collecting unit may be advantageous, since the use of a balloon facilitates delivery and since fluid may be used to stabilize the balloon and/or give some rigidity to the balloon. In one example, the balloon is filled with fluid upon or after delivery at the native valve.

Figures 12A, 12B:
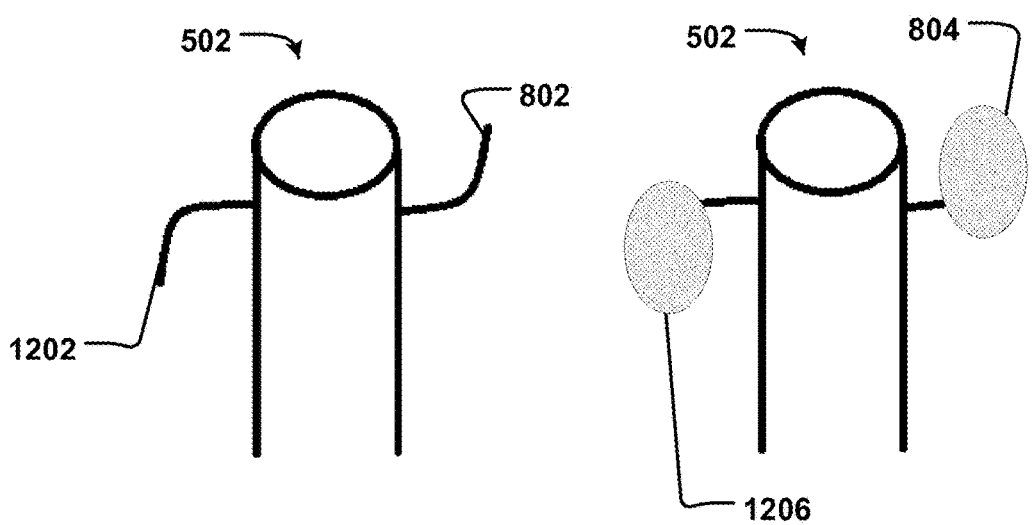
FIGS. 12A-B are schematic perspective views of a collecting unit for collecting and arranging chordae towards a valve, which unit comprises two hooks, arms or balloons.

FIG. 12A illustrates a collecting unit for collecting and arranging chordae towards the valve 502 according to some examples. In these examples the collecting unit comprises two hooks 802, 1202 or arms. Alternatively, the collecting unit comprises a plurality, such as four, of hooks or arms. The hooks or arms are preferably positioned equidistantly around the valve 502, i.e. the hooks or arms are preferably equidistantly distributed exteriorly along the valve 502. A collection unit comprising two fluid-fillable or fluid-filled balloons 804, 1206 is depicted in FIG. 12B. The collection unit may in addition to the fluid-fillable or fluid-filled balloons 804, 1206 comprise two arms. Alternatively, the collecting unit comprises a plurality, such as four, of fluid-fillable or fluid-filled balloons. The fluid-fillable or fluid-filled balloons are preferably positioned equidistantly around the valve 502, i.e. the fluid-fillable or fluid-filled balloons are preferably equidistantly distributed exteriorly along the valve 502.

In some examples, the collecting unit collects and arranges the chordae towards the valve 502 during rotation of the valve 502. The rotation is preferably anticlockwise rotation. The rotation of the valve 502 may be actuated by rotating a catheter, such as a two-axis steerable catheter. Thus, fast and easy collection of chordae may be achieved. Furthermore, fast and easy securing of the valve may be achieved. In addition, with a steerable catheter, fast and easy collection of chordae from outside the body of a patient may be achieved. Moreover, by specifying a direction of rotation, such as clockwise or anticlockwise, a procedure that is less prone to errors, and thus a faster and easier securing of the valve, may be obtained. In addition, reliable securing of the valve 502 and the chordae may be achieved.

In some examples, the valve 502 comprises a collecting unit for collecting and arranging leaflets towards the valve 502. In these examples, the valve 502 is secured, held and/or stabilized in a desired position by the collecting and arranging of leaflets towards the valve 502. In one example, the valve 502 is secured, held and/or stabilized in a desired position by the collecting and arranging of leaflets towards the valve 502 and by the collecting and arranging of chordae towards the valve 502. In some examples, the valve comprises a collecting unit for collecting and arranging chordae and leaflets towards the valve 502.

Figure 13A:
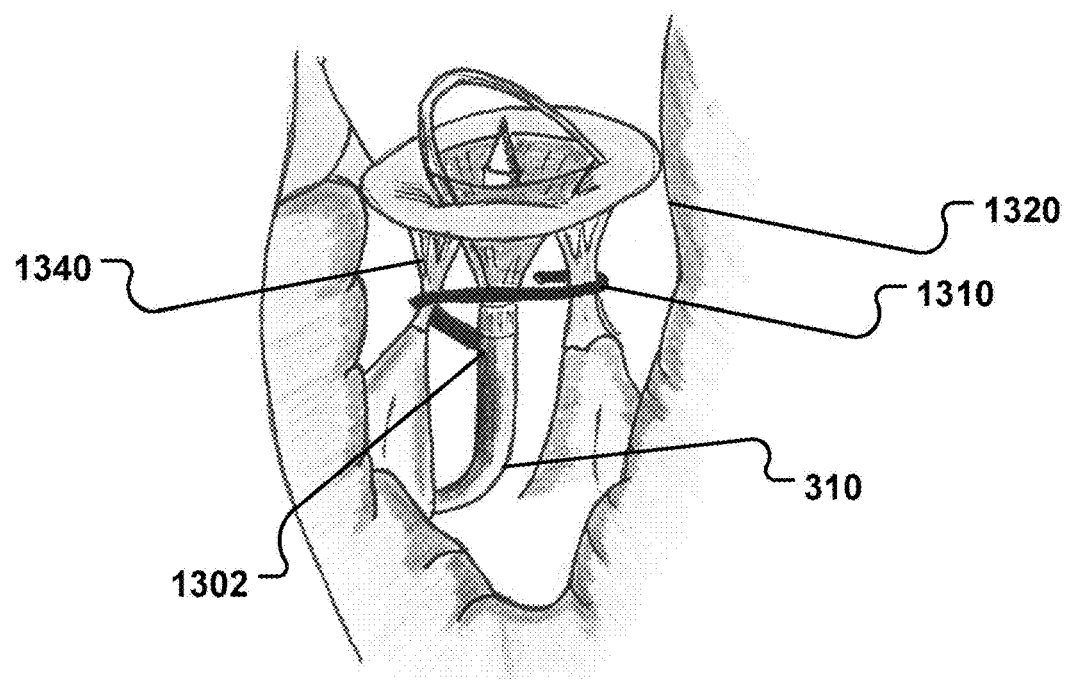
FIGS. 13A and 13B are schematic perspective views in partial cross-section which illustrate retracting of chordae.
Figure 13B:
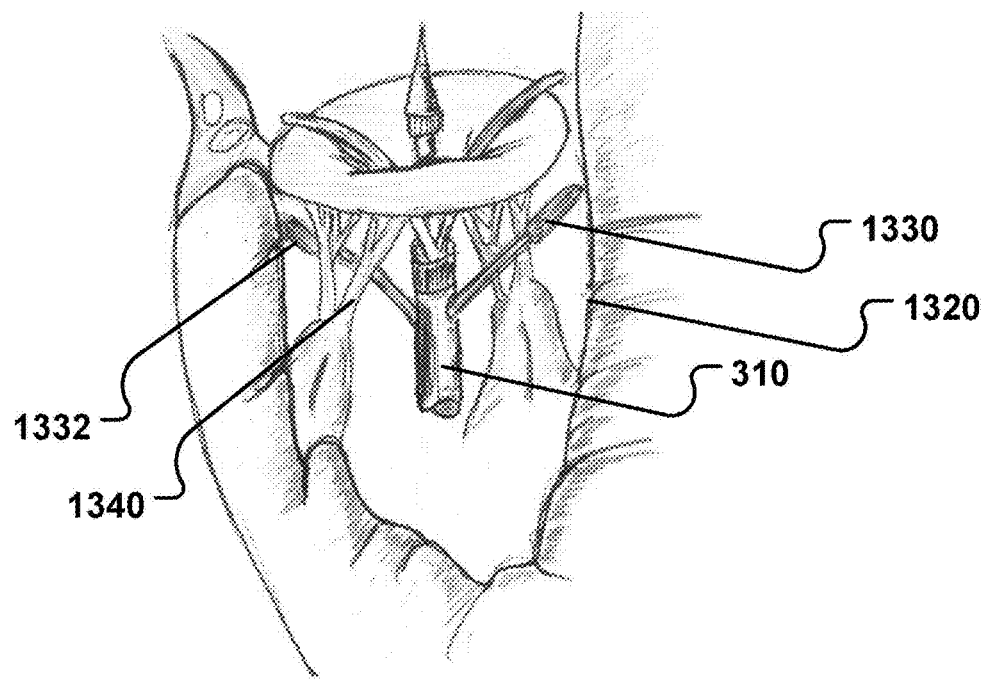

FIGS. 13A and 13B illustrate retracting of chordae. FIG. 13A illustrates retracting of chordae with a collection unit comprising a hook, an arm or a wire. A first end of a steerable catheter or wire 1310 exits a side lumen 1302 of the delivery catheter 310. The steerable catheter 1310 is then moved and manipulated by a user so as to surround the chordae 1340, without touching any ventricular wall 1320. The end of the catheter 1310 moves in a radial direction away from the delivery catheter 310 towards the ventricular wall 1320 as it is advanced and/or rotated. Once the catheter 1310 has encircled all the chordae 1340 and 360 degree coverage of the space is achieved, an end unit of the steering catheter or wire 1310 is activated to pull the chordae 1340 together. Activation may include rotation of the catheter or valve 502 whereupon the curvature of the end of the catheter having grasped the chordae pulls them together towards the valve. The delivery catheter 310 is held stationary during the whole deployment of the steerable catheter or wire 1310.

FIG. 13B illustrates retracting of chordae 1340 with a collection unit comprising two fluid-fillable or fluid-filled balloons. The delivery catheter 310 has two side lumens, which are equidistantly distributed around the delivery catheter 310, i.e. 180 degrees apart. The two balloon catheters 1330, 1332 exits the side lumens of the delivery catheter 310. The balloon catheters 1330, 1332 are then manipulated and moved towards a ventricular wall 1320 past the chordae 1340. Once the two balloon catheters are in position between the ventricular wall 1320 and the chordae 1340, the balloons may be inflated or filled with a fluid. When the balloons have been inflated or filled with a fluid, the balloons will fill the space between the ventricular wall 1320 and the chordae 1340 and press the chordae 1340 away from the ventricular wall and towards the centre and towards each other, i.e. the balloons will encapsulate the chordae 1340 and tighten the native valve and bring the chordae 1340 towards the delivery catheter 310. The surfaces of the balloons may be provided with grooves, which form hollow channels when the balloons are fully inflated or fluid-filled. These channels may then guide a ring or a replacement valve during deployment. Below, a medical system for short time replacement and repair of a native valve is described. The medical system comprises a valve 502. The valve 502 is in these examples an artificial valve. Furthermore, the medical system comprises a device for collecting and arranging chordae to hold and/or stabilize the artificial valve in a desired position. The device comprises a unit for grasping a plurality of chordae. With the medical system a fast and easy replacement of a native valve may be achieved. Furthermore, fast and easy positioning of a temporary artificial valve may be achieved. Moreover, use of the medical system may contribute to give more time to make decisions related to surgery, more time to prepare for surgery and/or more time to perform surgery/medical intervention. Thus, overall quality of e.g. valve replacement may be improved.

In some examples, the medical system comprises a steerable catheter for delivering the artificial valve; an annuloplasty device, which may be used to perform annuloplasty, i.e. to reshape the valve annulus, in order to improve the function of the valve; a location valve expander and/or a clip for locking the chordae in positions towards the artificial valve. This may enable fast and easy replacement of a native valve. Furthermore, it may enable fast and easy positioning of a temporary artificial valve.

Below, a device for collecting and arranging chordae to hold and/or stabilize an artificial valve in a desired position is described. The device may be a medical device, and comprises a unit for grasping a plurality of chordae. With the device, a fast and easy replacement of a native valve may be achieved. Furthermore, fast and easy positioning of a temporary artificial valve may be achieved. Moreover, use of the medical system may contribute to give more time to make decisions related to surgery, more time to prepare for surgery and/or more time to perform surgery/medical intervention. Thus, overall quality of e.g. valve replacement may be improved.

In some examples, the unit for grasping a plurality of chordae comprises an arm, a hook, a ring and/or a fluid-filled balloon. These examples provide for an easy way of grasping and/or collecting the chordae.

In some examples, the artificial valve is collapsible for delivery. Alternatively or in addition, the artificial valve may be expandable upon delivery. Furthermore, the device may be attachable to or integrable with the artificial valve. Thus, the device may be attached to or integrated with the artificial valve. These examples provide for an easier and less invasive delivery.

In some examples, the unit for grasping a plurality of chordae comprises a plurality of hooks. The number of hooks may be three, four or any other suitable number. Preferably, the hooks are positioned on opposite sides of the artificial valve. The hooks may also be equidistantly or symmetrically distributed exteriorly along the artificial valve.

In some examples, the catheter 310 enters from the groin and goes via a venous route transseptally to the right atrium 44 for delivery of the valve 502.

The medical system described herein may be utilized for short-term replacement of a native valve and/or for temporary use during beating heart surgery. The device described herein may be utilized for short-term replacement of a native valve and/or for temporary use during beating heart surgery. The valve 502 may be utilized during beating heart surgery. Thus, the system, the device and/or the valve 502 may enable beating heart surgery. Furthermore, the valve 502 may be utilized during life saving intervention, intervention in acute leaflet and/or chordate rupture.

The system, the device and or the valve 502 may provide for a reduced leakage and/or a minimized regurgitation during e.g. beating heart surgery. Furthermore, the system, the device and or the valve 502 may enable precise positioning of an implant or valve 502 in the anatomically correct position. Moreover, the procedure used for delivering a valve 502 described herein enables high accuracy of delivery, positioning and securing of a temporary valve 502.

Within this disclosure the term short-time or short-time replacement has been used. Short-term replacement and/or repair of native valves is considered to be a temporary replacement. Such a temporary replacement may be a replacement that last for minutes, hours or possibly up to a few days. Short-term replacement includes non-indwelling, i.e. non-permanently implanted, devices and methods described herein. Short-term replacement devices are intended to be removed from the body after use. With a long-time replacement is herein meant a replacement, which last for several days, weeks, months or longer. Such a long-time replacement may be made with devices intended to be permanently implanted and not removed from the body, such as indwelling annuloplasty devices. Structural requirements for such devices are thus different for short-term use and long-term use. As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present disclosure has been described above with reference to specific examples. However, other examples than the above described are equally possible within the scope of the disclosure. Different method steps or a different order thereof than those described above may be provided within the scope of the disclosure. The different features and steps of the disclosure may be combined in other combinations than those described. The scope of the disclosure is only limited by the appended patent claims.

The invention claimed is:

1. A medical system for short time replacement and repair of a native valve, comprising:
an artificial valve; and
a device for collecting and arranging chordae to hold and/or stabilize said artificial valve in a desired position, said device comprising:
a unit for grasping a plurality of chordae and/or leaflets, wherein said unit is a fluid-fillable balloon, whereby in use, said plurality of chordae is pulled towards the artificial valve by inflation of said unit, creating a temporary space between the chordae and the ventricular wall of the heart.

2. The system of claim 1, further comprising:
a steerable catheter for delivering said artificial valve; and/or
an annuloplasty device; and/or
a location valve expander; and/or
a clip for locking said chordae in positions towards said artificial valve.

3. The device of claim 1, wherein said artificial valve is collapsible for delivery and/or expandable upon delivery, and wherein said device is attached to or integrated with said artificial valve.

4. The device of claim 1, further comprising a clip.

5. The device of claim 4, wherein said chordae and/or said leaflets are kept in position towards said artificial valve with said clip.

6. The device of claim 4, wherein said clip is shaped as a helix.

7. A method of delivering an artificial valve for short time replacement of a native valve, such as a mitral valve or an aortic valve, in a heart, said method comprising:
positioning said artificial valve inside said native valve;
pulling a plurality of chordae and/or leaflets together and towards said artificial valve by use of a device for collecting and arranging chordae to hold and/or stabilize said artificial valve in a desired position, said device comprising:

a unit for grasping a plurality of chordae and/or leaflets, wherein said unit is a fluid-fillable balloon, whereby the method comprises:

pulling said plurality of chordae towards the artificial valve by inflation of said unit, creating a temporary space between the chordae and the ventricular wall of the heart.

8. The method of claim 7, further comprising: deploying a clip to surround said artificial valve and/or to keep said chordae and/or leaflets in position towards said artificial valve.

9. The method of claim 8 further comprising: deploying said clip by pushing it out of a catheter and into position with a pusher.

10. The method of claim 7, wherein said artificial valve is collapsible for delivery and/or expandable upon delivery.

11. The method of claim 7, wherein said catheter enters from the left ventricle and goes at least partly into the left atrium for delivery of said artificial valve.

12. The method of claim 11, wherein said catheter is a two-axis steerable catheter.

13. The method of claim 7, wherein a catheter enters from the groin and goes via aorta at least partly into the ascending aorta for delivery of said valve.

14. The method of claim 7, further comprising:
inserting an annuloplasty device; and
positioning said annuloplasty device.

15. The method of claim 14, wherein inserting of an annuloplasty device is performed after said artificial valve is positioned.

16. The method of claim 14, further comprising:
removing said artificial valve.

17. The method of claim 16, wherein said artificial valve is removed after said inserting and positioning of said annuloplasty device.

18. The method of claim 7, further comprising:
advancing an annuloplasty device into position through said temporary space.

* * * * *